（12) United States Patent
Kudoh et al.

(10) Patent No.: US 8,523,766 B2
(45) Date of Patent: Sep. 3, 2013

(54) ENDOSCOPE

(75) Inventors: Yoshimitsu Kudoh, Kanagawa (JP);
Tsuyoshi Ashida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 534 days.

(21) Appl. No.: 12/723,611

(22) Filed: Mar. 12, 2010

(65) Prior Publication Data

US 2011/0065994 A1    Mar. 17, 2011

(30) Foreign Application Priority Data

Mar. 18, 2009    (JP) ................. P2009-065932

(51) Int. Cl.
*A61B 1/00* (2006.01)
*G02B 23/24* (2006.01)

(52) U.S. Cl.
USPC ..................... 600/146; 600/118; 600/145

(58) Field of Classification Search
USPC .............. 128/662.06; 600/118, 146, 150
See application file for complete search history.

(56) References Cited

U.S. PATENT DOCUMENTS

| | | | | |
|---|---|---|---|---|
| 4,726,355 | A * | 2/1988 | Okada | 600/114 |
| 4,928,699 | A * | 5/1990 | Sasai | 600/463 |
| 5,431,645 | A * | 7/1995 | Smith et al. | 606/1 |
| 5,518,163 | A * | 5/1996 | Hooven | 227/5 |
| 5,656,011 | A * | 8/1997 | Uihlein et al. | 600/146 |
| 6,432,043 | B2 * | 8/2002 | Nakaichi et al. | 600/120 |
| 6,551,237 | B2 * | 4/2003 | Matsui | 600/118 |
| 6,702,737 | B2 * | 3/2004 | Hino et al. | 600/146 |
| 6,817,973 | B2 * | 11/2004 | Merril et al. | 600/118 |
| 6,932,761 | B2 * | 8/2005 | Maeda et al. | 600/152 |
| 7,041,053 | B2 * | 5/2006 | Miyake | 600/146 |
| 7,179,223 | B2 * | 2/2007 | Motoki et al. | 600/131 |
| 7,214,183 | B2 * | 5/2007 | Miyake | 600/131 |
| 7,751,937 | B2 * | 7/2010 | Sabe et al. | 700/245 |
| 7,758,613 | B2 * | 7/2010 | Whitman | 606/219 |
| 7,819,799 | B2 * | 10/2010 | Merril et al. | 600/118 |

(Continued)

FOREIGN PATENT DOCUMENTS

| | | |
|---|---|---|
| JP | 5-329097 A | 12/1993 |
| JP | 2005-28018 A | 2/2005 |
| JP | 2005-28018 A | 2/2005 |

OTHER PUBLICATIONS

Extended European Search Report Jun. 7, 2010.

(Continued)

*Primary Examiner* — Clayton E LaBalle
*Assistant Examiner* — Kevin Butler
(74) *Attorney, Agent, or Firm* — McGinn Intellectual Property Law Group, PLLC

(57) ABSTRACT

The endoscope is equipped with: a curving manipulation unit provided on the main body manipulating unit, for performing a manual operation which causes the curving portion; a curving drive unit for coupling the curving manipulation unit to the curving portion so as to curve the curving portion in response to a manipulation performed by the curving manipulation unit; a manipulating force detecting unit for detecting a manipulating force applied to the curving manipulation unit; a manipulation assisting power calculating unit for calculating manipulation assisting power corresponding to the manipulating force detected by the manipulating force detecting unit; and a rotation driving force generating unit for applying a driving force via a driving force transferring mechanism to the curving drive unit, so as to generate the manipulation assisting power calculated by the manipulation assisting power calculating unit; in which the rotation driving force generating unit is arranged in an appendix unit.

17 Claims, 12 Drawing Sheets

(56) References Cited

U.S. PATENT DOCUMENTS

| | | | |
|---|---|---|---|
| 2002/0143238 A1* | 10/2002 | Hino et al. | 600/146 |
| 2004/0049097 A1* | 3/2004 | Miyake | 600/150 |
| 2006/0195227 A1* | 8/2006 | Sabe et al. | 700/245 |
| 2007/0161861 A1* | 7/2007 | Kawai et al. | 600/145 |
| 2008/0249365 A1* | 10/2008 | Masaki | 600/152 |
| 2010/0113879 A1* | 5/2010 | Fukunaga | 600/140 |
| 2011/0065994 A1* | 3/2011 | Kudoh et al. | 600/146 |
| 2011/0237891 A1* | 9/2011 | Sato et al. | 600/149 |

OTHER PUBLICATIONS

Japanese Office Action dated Feb. 26, 2013 with partial English translation thereof.

* cited by examiner

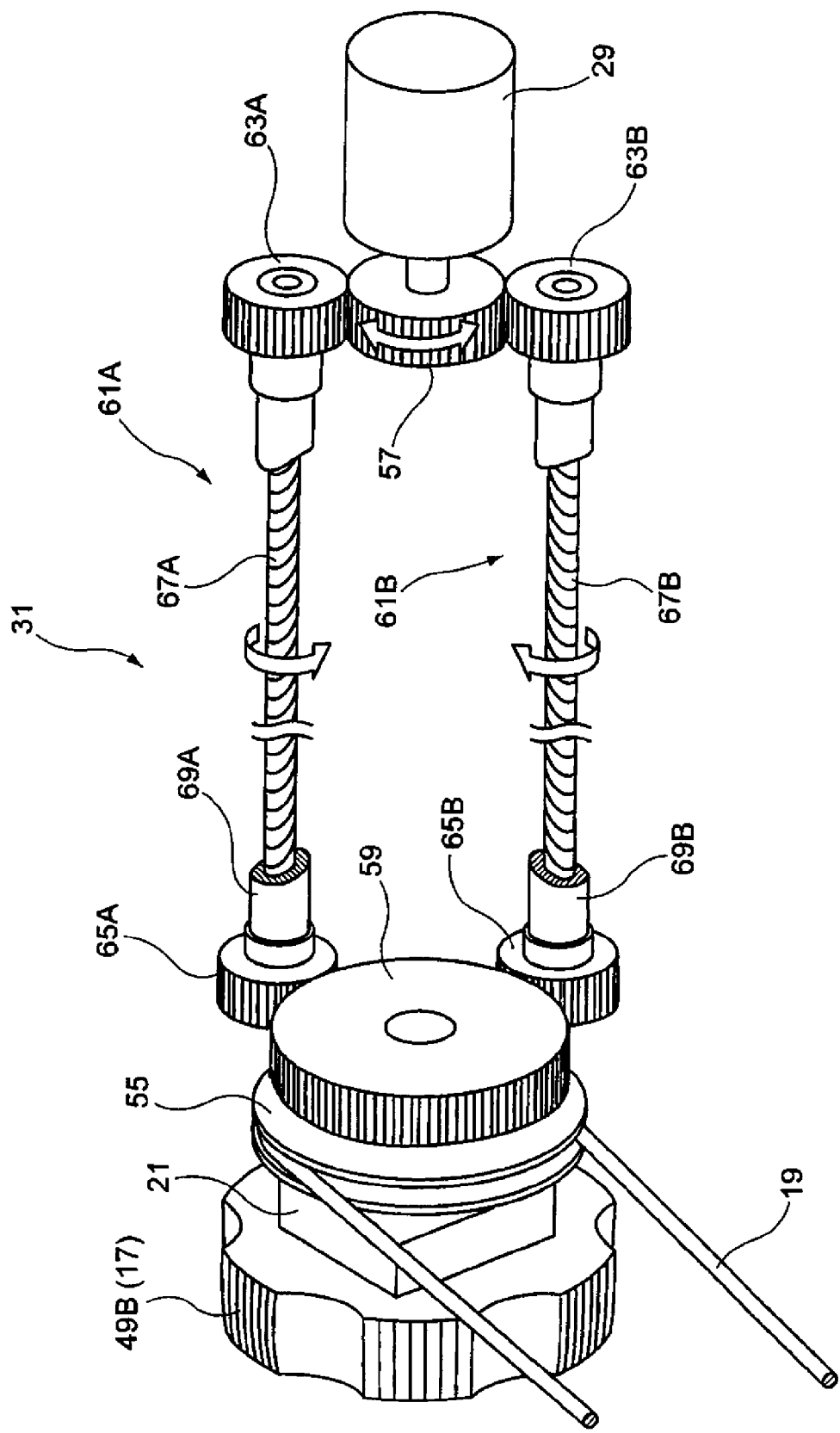

ENDOSCOPE

CROSS-REFERENCE TO RELATED APPLICATIONS

This application claims the benefit of Japanese Patent Application No. 2009-065932, filed on Mar. 18, 2009, the entire contents of which are hereby incorporated by reference, the same as if set forth at length, the entire of which are incorporated herein by reference.

BACKGROUND OF THE INVENTION

1. Technical Field

The present invention relates to an endoscope having a curving portion at a tip of an endoscope inserting portion.

2. Description of Related Art

Endoscopes have been widely utilized as apparatuses capable of viewing inner portions of body cavities, inner portions of tubes of structural objects, and the like. While endoscopes are equipped with endoscope inserting portions which are inserted into inner portions of objects under inspection and main body manipulating units provided to be communicated with base ends of the endoscope inserting portions, curving portions are provided on the side of tips of the endoscope inserting portions and are curved by hauling manipulation wires penetrated through the endoscope inserting portions. The manipulation wires are hauled along desirable directions by manipulating angle knobs arranged on main body manipulating units, so that the curving portions can be curved along the desirable directions. Among the above-described endoscopes, such an endoscope equipped with a power assist function has been described in JP-A-2005-028018. That is, in order to reduce manipulating forces capable of curving the curving portion in the power assist function of the endoscope, manipulation assisting power for assisting to haul the manipulation wire are applied to a wire hauling member by operating an assist-purpose driving motor. In accordance with the above-described endoscope having the power assist function, since the manipulation assisting power generated by the driving motor provided in the main body manipulating unit is applied to the angle knob in addition to manipulating forces for the angle knob which are produced by an operator of this endoscope, the curving portion can be curved only by a desirable curving amount while the manipulating forces are reduced.

SUMMARY

The present invention has an object to provide an endoscope capable of achieving a power assist function having superior operability without increasing a size and weight of a main body manipulating unit even in such a case that manipulation assisting power is furthermore increased and are generated in higher precision.

An endoscope includes an endoscope inserting unit, a main body manipulating unit, an appendix unit, a curving manipulation unit, a curving drive unit, a manipulating force detecting unit, a manipulation assisting power calculating unit and a rotation driving force generating unit. The endoscope inserting unit is to be inserted into an inner portion of an object under inspection, and has a freely curvable curving portion in a vicinity of a tip portion of the endoscope inserting unit. The main body manipulating unit is provided to be connected to a base end side of the endoscope inserting unit. The appendix unit is connected via a flexible softened portion to the main body manipulating unit. The curving manipulation unit is provided on the main body manipulating unit, and is manually operated for causing the curving portion to be curved along a direction. The curving drive unit couples the curving manipulation unit to the curving portion so as to curve the curving portion in response to a manipulation performed on the curving manipulation unit. The manipulating force detecting unit detects a manipulating force applied to the curving manipulation unit. The manipulation assisting power calculating unit calculates manipulation assisting power corresponding to the manipulating force detected by the manipulating force detecting unit. The rotation driving force generating unit applies a driving force via a driving force transferring mechanism to the curving drive unit so as to generate the manipulation assisting power calculated by the manipulation assisting power calculating unit. The rotation driving force generating unit is arranged in the appendix unit.

In accordance with the endoscope of the present invention, since the rotation driving force generating unit for generating the manipulation assisting power is arranged in the appendix unit connected via the softened portion to the main body manipulating unit, in such a case that the manipulation assisting power having the large magnitudes are generated in high precision, even when the dimension of the rotation driving force generating unit is increased, the manipulation assisting power can be applied to the curving manipulation unit without deteriorating operability, while the sizes and the weight of the main body manipulating unit and the endoscope inserting portion are not increased. As a consequence, the power assist function having the superior operability and capable of reducing manipulation fatigue of the operator can be achieved.

BRIEF DESCRIPTION OF THE DRAWINGS

FIG. 4 is an explanatory diagram for schematically showing a concrete structure of a driving force transferring mechanism.

DETAILED DESCRIPTION OF EMBODIMENTS OF THE INVENTION

Referring now to drawings, a detailed description is made of an embodiment mode of the present invention.

Figure 1:
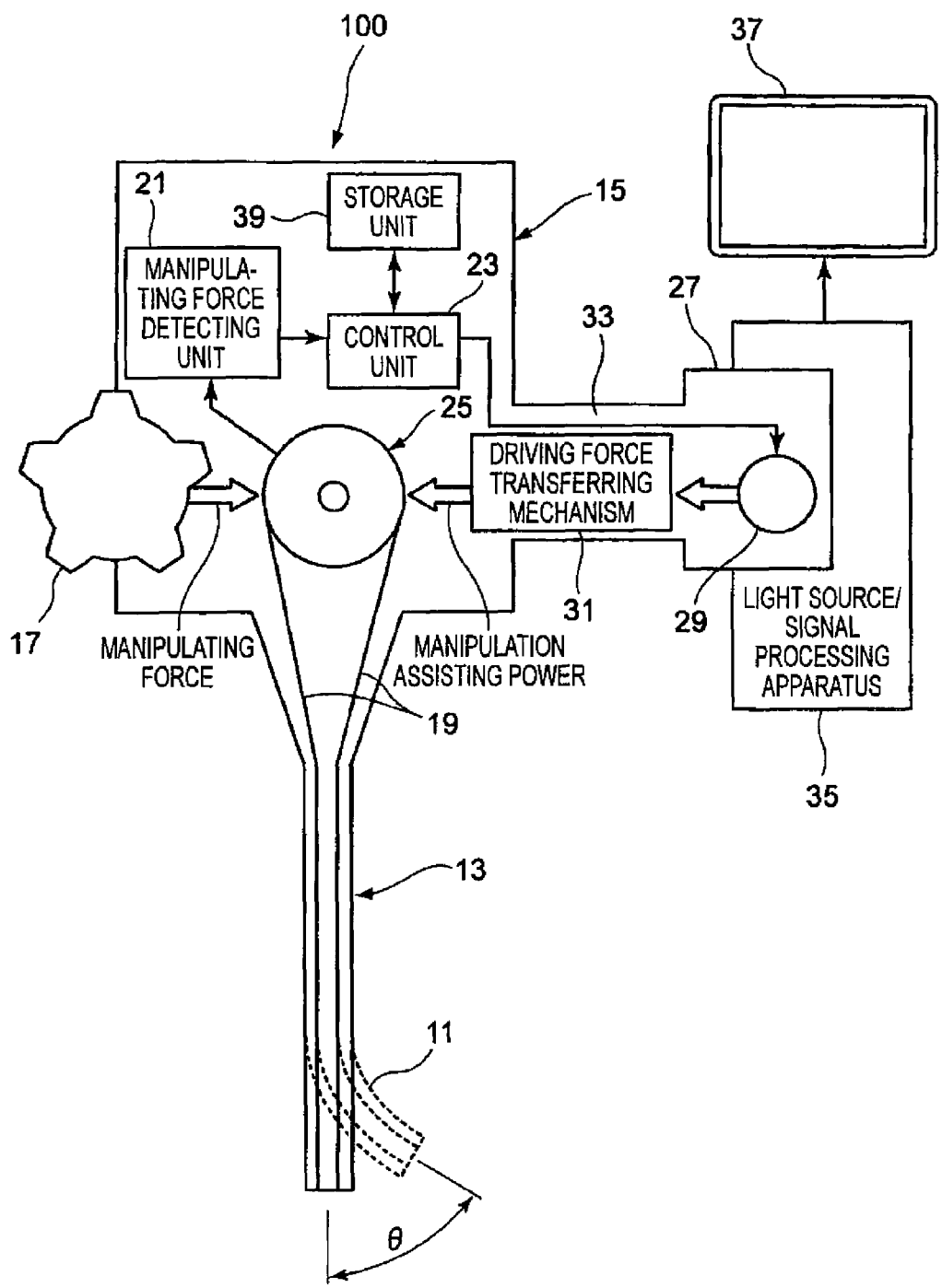
FIG. 1 is a diagram for explaining an embodiment mode of the present invention, i.e., a structural block diagram for schematically indicating an endoscope and an endoscope system containing the endoscope.

FIG. 1 is a diagram for explaining the embodiment mode of the present invention, i.e., a structural block diagram for schematically indicating an endoscope and an endoscope system containing the endoscope.

As shown in this drawing, an endoscope 100 of the present embodiment mode is equipped with an endoscope inserting portion 13 having a curving portion 11, and a main body manipulating unit 15. The endoscope inserting portion 13 is inserted into an object under inspection (not shown), while the curving portion 11 which can be freely curved is provided in the vicinity of a tip portion thereof. The main body manipulating unit 15 is provided to be connected to a base end side of the endoscope inserting portion 13.

The main body manipulating unit 15 has a curving manipulation unit 17 by which an operator of the endoscope 100 performs a manual operation for curving the curving portion 11 along a desirable direction. One pair of manipulation wires 19 internally inserted along the endoscope inserting portion 13 are hauled and/or fed out by manipulating the curving manipulation unit 17. Since the manipulation wires 19 are hauled and/or fed out, the curving portion 11 is curved along the desirable direction, so that a viewing direction of the endoscope 100 can be changed.

Also, manipulating forces applied by the operator to the curving manipulation unit 17 are detected by a manipulating force detecting unit 21, and a control unit 23 applies manipulation assisting power to a curving drive unit 25, which correspond to the manipulating forces detected by the manipulating force detecting unit 21. The endoscope 100 of the present embodiment mode has a power assist function in order to reduce manual manipulating forces which are required to curve the curving portion 11, and are applied to the curving manipulation unit 17. The above-described power assist function generates manipulation assisting power for assisting traction of the manipulation wires 19, and applies the generated manipulation assisting power to the curving drive unit 25 connected to the curving manipulation unit 17.

The above-described manipulation assisting power is obtained by that in response to an instruction of the control unit 23, a driving motor 29 is rotationally driven which corresponds to a rotation driving force generating unit arranged in a connecting connector 27, and then, the rotating forces of the driving motor 29 are transferred via a driving force transferring mechanism 31 to the curving drive unit 25. In this case, the connecting connector 27 is connected via a flexible light guide (LG) softened portion 33 to the main body manipulating unit 15, and corresponds to an appendix unit which is separately arranged with respect to the main body manipulating unit 15.

While the above-described connecting connector 27 is connected to a light source/signal processing apparatus 35, the light source/signal processing apparatus 35 supplies illumination light with respect to an illumination optical system (not shown) and an imaging optical system (not shown) containing an imaging element, which are arranged in a tip of the endoscope inserting portion 13, and inputs thereinto signals of viewing images derived from the imaging element. The light source/signal processing apparatus 35 performs a proper signal process with respect to the viewing images outputted from the endoscope 100, and then, displays the processed viewing images on a monitor 37. As previously described, the above-described endoscope system containing the endoscope 100, the light source/signal processing apparatus 35, and the monitor 37 can acquire a desirable viewing image by operating the endoscope 100 having the power assist function of the curving manipulation, and can perform an image diagnosis based upon the acquired viewing image. It should be understood that while a storage unit 39 which has previously stored thereinto various sorts of parameters (will be described later) is connected to the control unit 23, the control unit 23 may furthermore function as a manipulation assisting power calculating unit for calculating manipulation assisting power corresponding to a detected manipulating force.

In this case, a description is made of the power assist function for curving manipulations.

Figure 2:
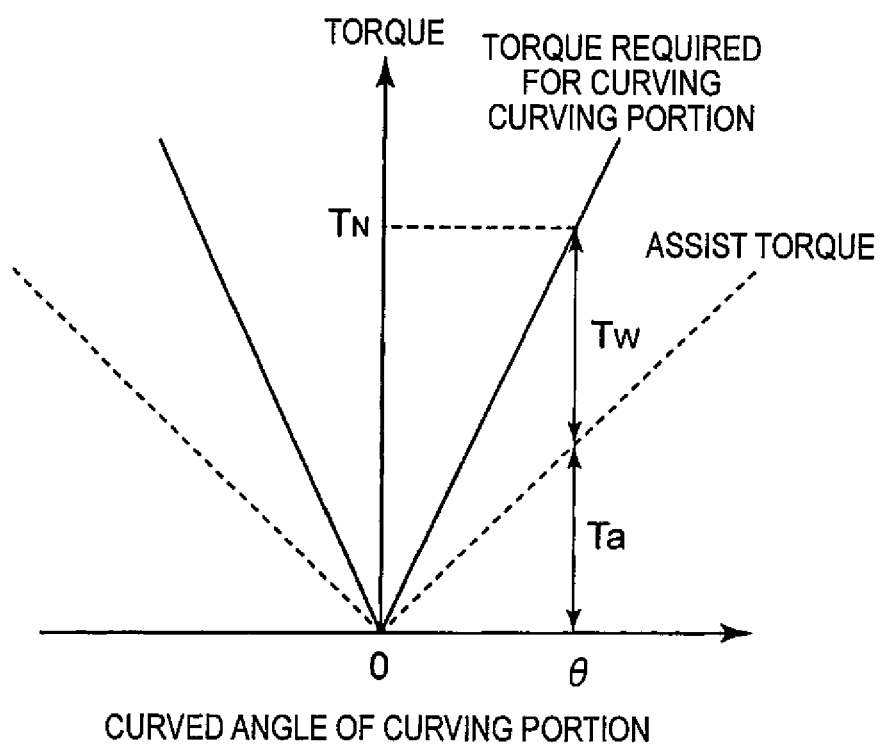
FIG. 2 is an explanatory diagram for showing a relationship between a curved angle of a curving portion and rotation torque generated in a curving drive unit.

FIG. 2 shows a relationship between curved angles of the curving portion 11 and rotation torque generated in the curving drive unit 25. In order that the tip of the endoscope inserting portion 13 is curved at a certain curved angle "θ" by the curving portion 11, predetermined torque "TN" is required to be applied to the curving drive unit 25. In the conventional endoscope system, the operator has manipulated the curving portion 11 by applying all the torque "TN" to the curving manipulation unit 17. In such a case, the manipulation loads given to the operator is heavy, so that reaction forces received when the endoscope inserting portion 13 abuts against a tubular wall of a body cavity can be hardly sensed in a delicate manner by finger tips to be manipulated. As a consequence, if the power assist function for the curving manipulations is employed, then the manipulation loads given to the operator can be reduced so as to firmly perceive the reaction forces received from the tubular wall of the body cavity, so that operability and precise characteristics of diagnoses can be improved. More specifically, in the case that the tip of the endoscope inserting portion 13 is curved at a larger angle, and is wanted to be more precisely curved, the effects of the above-described power assist function may be increased, and merits of the power assist function may be obtained.

Concretely speaking, in the case that the curved angle "θ" is selected, while torque required for endoscope manipulations by the operator within the torque "TN" required for the curving manipulations is assumed as "Tw", since the remaining torque "Ta" is assisted by manipulation assisting power, the torque "Tw" by which the operator manipulates the curving portion 11 is reduced. The assist torque "Ta" produced by manipulation assisting power is different for each other in response to curved angles of the curving portion 11, and is set in such a mariner that the assist torque "Ta" does not exceed the required torque "TN." Since the assist torque "Ta" is set to become continuously smaller than the required torque "TN", reaction forces received by the endoscope inserting portion 13 during curving manipulations may be perceived by hands of the operator.

In accordance with the endoscope 100 having the above-described structure, since the driving motor 29 for generating the manipulation assisting power is arranged in the connecting connector 27 connected via the LG softened portion 33 to the main body manipulating unit 15 shown in FIG. 1, sizes and weight of the main body manipulating portion 15 and the endoscope inserting portion 13 are not increased due to the driving motor 29, but the manipulation assisting power can be generated while the operability is kept high. In other words, in such a case that the manipulation assisting power is wanted to be furthermore increased, or is wanted to be generated in higher precision, even when performance of the driving motor 29 is increased, or a dimension of a driving mechanism (not shown) connected to the driving motor 29 is made large, since the driving motor 29 has been separately arranged with respect to the main body manipulating unit 15 and the endoscope inserting portion 13, the operability of the endoscope 100 is not deteriorated. As a result, the power assist function having the superior operability and capable of reducing manipulation fatigue of the operator can be realized.

It should be understood that in the above-explained structural example, the power assist of the endoscope 100 has been carried out by employing the manipulating force detecting unit (torque sensor) 21. However, the present invention is not limited only to the above-described structural example, but may be alternatively realized by such a power assist performing arrangement that curved angles of the curving portion 11 may be calculated by a rotation angle sensor, and the like, which detects move amounts of the manipulation wires 19, and rotation angles of angle knobs 49A and 49B.

Next, an endoscope equipped with the above-described basic structure is more concretely described based upon one application example. In this application example, although an electronic endoscope designed for digestive organs is exemplified, the present invention is not limited only to the above-described electronic endoscope, but may be alternatively applied to other medical-purpose endoscopes, or industrial-purpose endoscopes.

Figure 3:
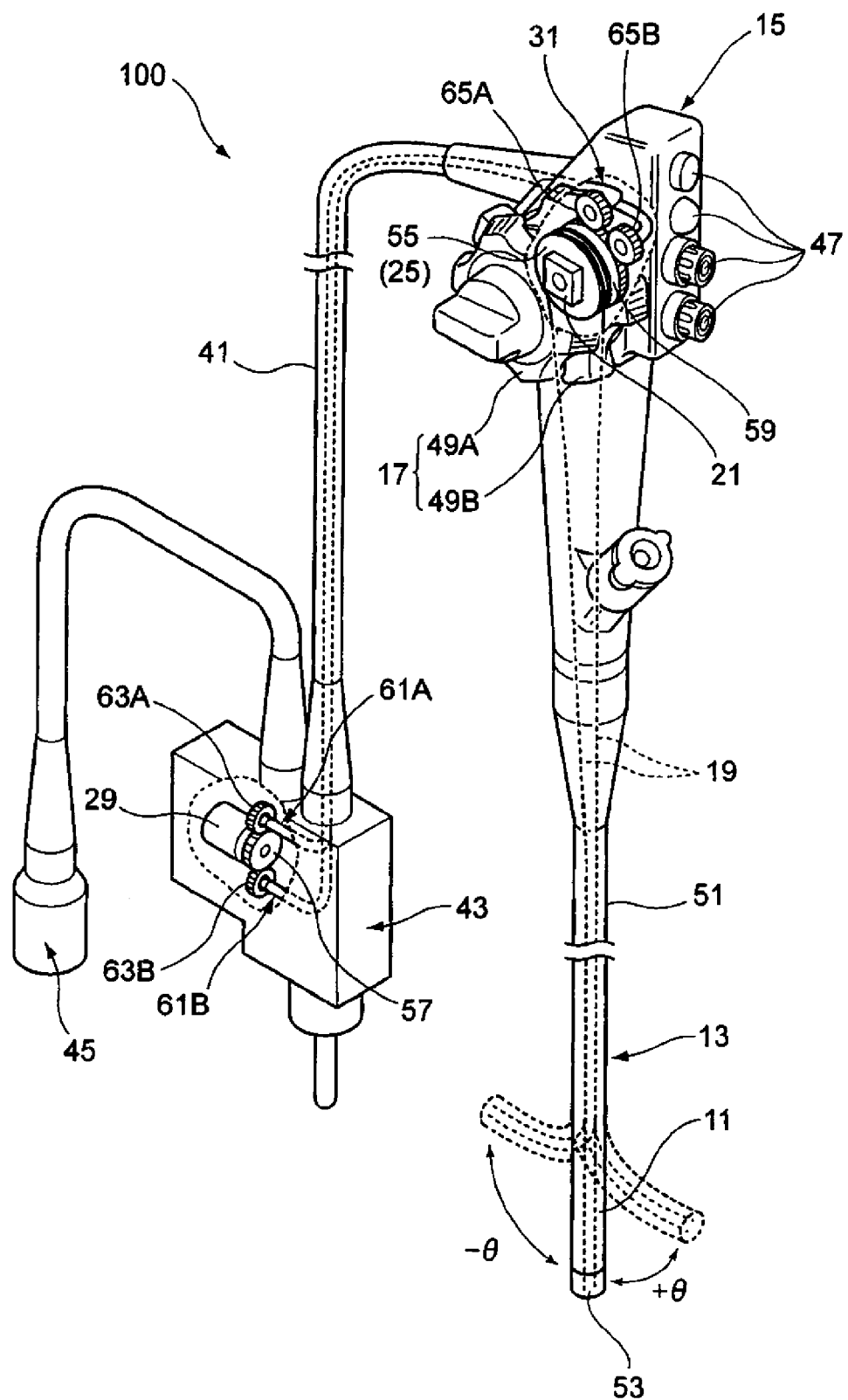
FIG. 3 is a perspective view for indicating an entire construction of the endoscope as one example.

FIG. 3 is a perspective view for showing the entire structure of the endoscope 100 as one example.

The endoscope 100 is equipped with the main body manipulating unit 15 and the endoscope inserting portion 13 which is provided to be communicated with the main body manipulating unit 15 and is inserted into an object under inspection (not shown). While a universal cord 41 which constitutes a flexible LG softened portion is connected to the main body manipulating unit 15, a light guide (LG) connector 43 functioning as a connecting connector is arranged at a tip of the universal cord 41. Also, a video connector 45 functioning as another connecting connector is connected to the LG connector 43. The LG connector 43 is connected to an optical source apparatus (not shown) so as to conduct illumination light to the tip of the endoscope inserting portion 13, and the video connector 45 is connected to a signal processing apparatus (not shown) which performs an image process in order to output acquired viewing images to the signal processing apparatus.

Also, various sorts of manipulation buttons 47 are additionally provided on the main body manipulating unit 15 of the endoscope 100, and further, one pair of angle knobs 49A and 49B corresponding to the curving manipulation unit 17 are provided thereon. As to the above-described manipulation buttons 47, buttons are employed in order to perform sucking operation, air feeding operation, and water feeding operation on the tip side of the endoscope inserting portion 13, and a shutter button is employed when an imaging operation is carried out.

The endoscope inserting portion 13 is constructed of a softened portion 51, the curving portion 11, and a tip portion 53, which are successively located in this order from the side of the main body manipulating unit 15. As previously described, the curving portion 11 is remotely curving-manipulated by pivotally rotating the angle knobs 49A and 49B of the main body manipulating unit 15, so that the tip portion 53 can be directed toward a desirable curving direction. In other words, the curving portion 11 is curved along a direction (will be referred to as "right/left curving direction" hereinafter) indicated by a dotted line in FIG. 3 by pivotally rotating the angle knob 49B, whereas the curving portion 11 is curved along a direction (will be referred to as "upper/lower curving direction" hereinafter) which is orthogonally intersected to the above-described right/left curving direction by pivotally rotating the angle knob 49A.

The curving manipulation of the curving portion 11 is carried out by manipulating one pair of the manipulation wires 19 internally inserted along the endoscope inserting portion 13, while the angle knobs 49A and 49B are separately connected to a pulley 55, and cause the manipulation wire 19 wound on this pulley 55 to be hauled and/or fed out. For the sake of a simple explanation in FIG. 3, only one system is illustrated which is arranged by the pulley 55 connected to the angle knob 49B, and the manipulation wire 19 wound on the pulley 55. However, the endoscope 100 has been actually equipped with two systems (in total) of curving manipulation mechanisms in which a pulley, manipulation wires, and the like are similarly provided with respect to the angle knob 49A. Then, the above-described pulley 55 and manipulation wires 19 function as a curving drive unit 25.

Both end portions of one manipulation wire 19 are fixed on the tip portion 53 of the endoscope inserting portion 13, and a loop portion of this manipulation wire 19 which is located on the opposite side from the tip portion 53 is wound on the pulley 55. Since this pulley 55 is pivotally driven by pivotally rotating the angle knob 49B, the manipulation wire 19 is hauled and/or fed out, so that the curving portion 11 may be curved.

Next, a description is made of the driving force transferring mechanism 31 for transferring rotating forces of the driving motor 29 to the pulley 55.

While the driving force transferring mechanism 31 is provided in such a manner that the main body manipulating unit 15 is coupled to the LG connector 43, the driving force transferring mechanism 31 has an input-sided gear 57 provided on a rotation driving shaft of the driving motor 29, and an output-sided gear 59 which pivotally rotates the pulley 55, and the input-sided gear 57 is coupled to the output-sided gear 59 by at least two wire members 61A and 61B. One end side of each of the wire members 61A and 61B is connected to driving gears 63A and 63B, respectively, which are meshed with the input-sided gear 57, whereas the other end side of each of the wire members 61A and 61B is connected to driven gears 65A and 65B, respectively, which are meshed with the output-sided gear 59.

Also, the angle knob 49B, the pulley 55, and the output-sided gear 59 are integrally connected to each other on the same axes. A manipulating force for pivotally rotating the angle knob 49B in a manual manner is detected by a torque sensor 21 corresponding to a manipulating force detecting unit.

Referring now to FIG. 4, a description is made of a concrete structure of the above-described driving force transferring mechanism 31 schematically shown in this drawing. It should be understood that the same reference numerals shown in FIG. 3 will be employed as those for denoting the same structural members in the below-mentioned descriptions, and thus, explanations of the same structural members will be made simpler, or omitted.

As shown in FIG. 4, the wire members 61A and 61B are flexible shafts having outer tubes 69A and 69B, while wires 67A and 67B are provided as core members, which are manufactured by twisting a large number of narrow wires along a specific twisting direction. The outer tubes 69A and 69B freely rotatably cover the wires 67A and 67B on outer circumferential portions of these wires 67A and 67B. It should be understood that although the wires 67A and 67B have been illustrated in the drawing by exposing a portion thereof, these wires 67A and 67B have been covered over their entire lengths by the outer tubes 69A and 69B.

When the driving motor 29 rotatably drives the input-sided gear 57, the driving gears 63A and 63B meshed with the input-sided gear 57 are driven to be rotated, and thus, the driven gears 65A and 65B are rotatably driven via the wire members 61A and 61B so as to pivotally rotate the output-sided gear 59, while the wire members 61A and 61B are under joint condition to the driving gears 63A and 63B respectively. As a result, rotating forces are applied to the pulley 55, so that manipulation assisting power for curving the curving portion 11 (refer to FIG. 1) are applied to the manipulation wire 19.

Figure 5A:
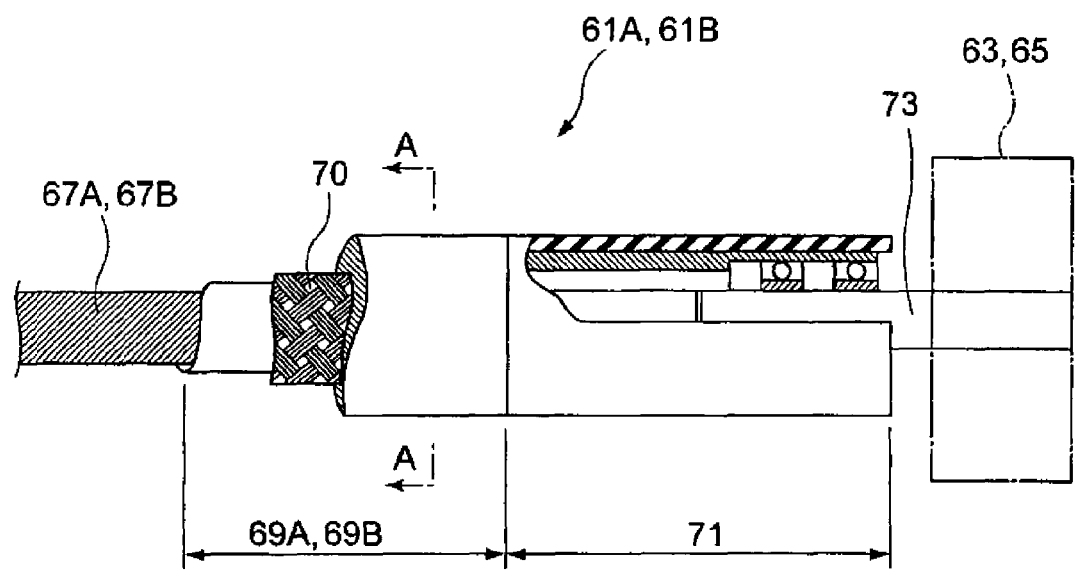
FIG. 5A is a partially sectional structural diagram for showing an internal structure of an end portion of a wire member.
Figure 5B:
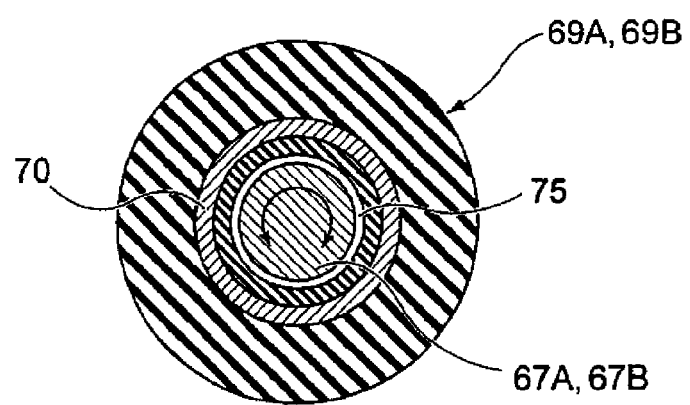
FIG. 5B is a sectional view for indicating the internal structure, taken along a line A-A of FIG. 5A.

FIG. 5A is a partially sectional structural diagram for indicating an internal structure of an end portion of the wire member 61A, or 61B, and FIG. 5B is a sectional view of the internal structure, taken along a line A-A of FIG. 5A.

The wire members 61A and 61B have wires 67A and 6713 which constitute freely rotatable inner shafts, and outer tubes 69A and 69B, while a rotation shaft 73 connected to the wires 67A and 67B and supported by a gear portion 71 is provided at an end portion of each of the wire members 61a and 61B. In the outer tubes 69A and 69B, for instance, both an inner surface and an outer surface of a mesh wire 70 are covered by a resin material. This rotation shaft 73 is connected to the driving gears 63A, 63B, and the driven gears 65A, 65B. Also, a lubricating agent 75 such as grease has been filled into gaps between the outer circumferential planes of the wires 67A, 67B, and the inner circumferential planes of the outer tubes 69A and 69B.

As previously described, since the wires 67A and 67B are covered by the outer tubes 69A and 69B, the wires 67A and 67B can firmly transfer the supplied rotating forces to the counter-sided components without interfering with other components.

As shown in FIG. 4, in the wires 67A and 67B corresponding to the inner shafts, the twisting directions along which large numbers of narrow wires are stranded are set to mutually different directions in outermost layers thereof. Generally speaking, while an inner shaft has been manufactured by winding wires of plural layers on a single wire, a left rotation-purpose inner shaft, and a right rotation-purpose inner shaft are present, depending upon a twisting direction of an outermost layer of the wires. If the twisting direction of the outermost layer of the wires is made coincident with a rotation direction, then the resulting inner shaft can be strengthened with respect to twists, rotation precision is increased, and also, both an angular error along the twisting direction of the wires and aged deterioration thereof are reduced. In the structural example of the present embodiment mode, even when a rotation direction of the driving motor 29 is either the normal rotation direction or the reverse rotation direction, since a twisting direction of an outermost layer of any of the wires 67A and 67B is coincident with the rotation direction, rotation driving forces can be transferred in higher angle precision.

It should also be noted that a total number of the above-described wire members 61A and 61B is not limited only to two, but three, or more pieces of wire members 61A and 61B may be alternatively employed, if necessary. Since total numbers of these wire members 61A and 61B are increased, larger driving forces may be transferred, so that aged deterioration may be reduced and rotation precision may be furthermore increased.

Next, rotation driving operation of the pulley 55 by the above-described driving force transferring mechanism 31 is described in detail.

Figure 6A:
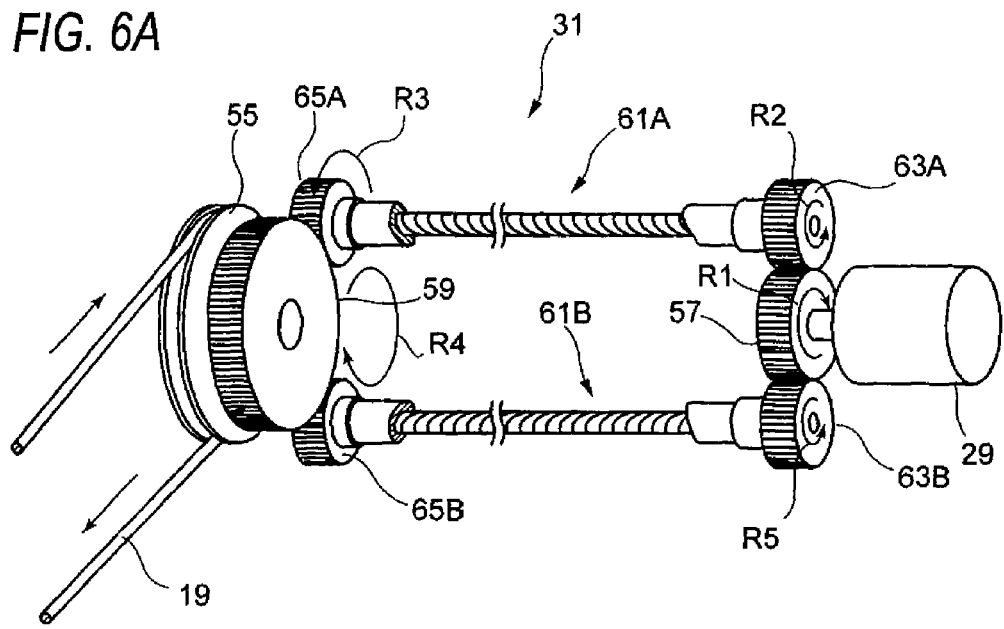
FIG. 6A and FIG. 6B are explanatory diagrams for representing transferring conditions of rotating forces transferred by the driving force transferring mechanism.
Figure 6B:
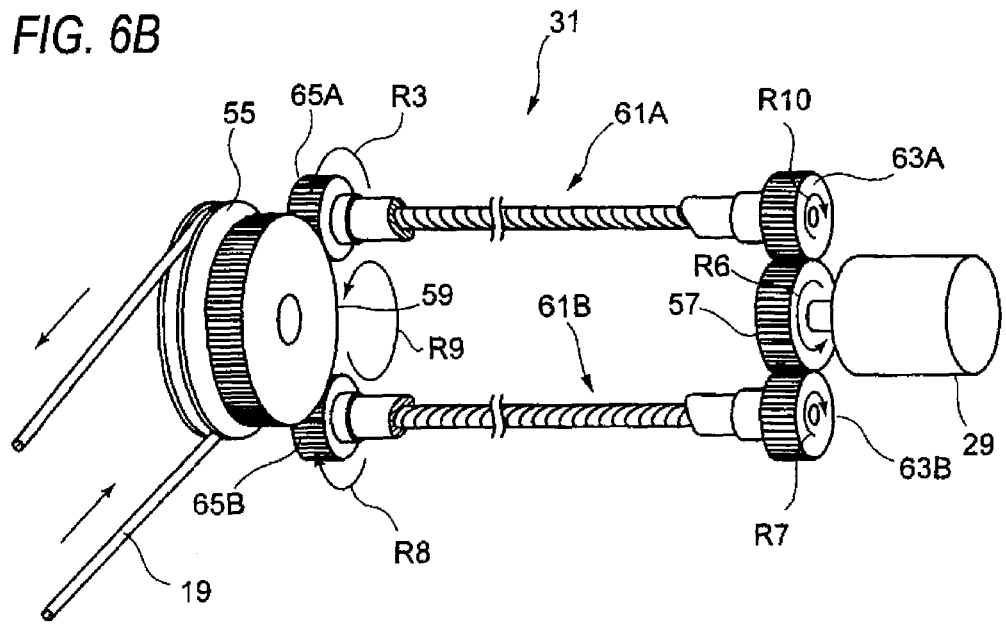

FIG. 6A and FIG. 6B are explanatory diagrams for representing transferring conditions of rotating forces by the driving force transferring mechanism 31. As indicated in FIG. 6A, when the driving motor 29 is driven so as to rotate the input-sided gear 57 along a direction "R1", the driving gear 63A is rotated along a direction "R2", and thus, drives the driven gear 65A via the wire member 61A along a direction "R3." As a result, the output-sided gear 59 is rotated along a direction "R4" so as to rotate the pulley 55, so that the manipulation wire 19 is hauled and fed out as indicated by arrows in the drawing. At this time, since the rotation direction of the driving gear 63A is presently coincident with the twisting direction of the wire member 61A at the outermost wire layer (refer to FIG. 4), the rotating forces supplied from the driving motor 29 are firmly transferred to the output-sided gear 59 in high precision.

On the other hand, the driving gear 63B is rotated along a direction "R5", and the rotating forces of this driving gear 63B are transferred via the wire member 61B and the driven gear 65B to the output-sided gear 59. However, in this case, since the rotation direction is a reverse direction as to the twisting direction of the wire member 61B at the outermost wire layer, a transfer efficiency is low and the driving forces transferred by the wire member 61A occupy a dominant position.

Also, as represented in FIG. 6B, when the driving motor 29 is driven so as to rotate the input-sided gear 57 along a direction "R6" which is directed opposite to the above-described direction "R1", the driving gear 63B is rotated along a direction "R7", and thus, drives the driven gear 65B via the wire member 61B along a direction "R8." As a result, the output-sided gear 59 is rotated along a direction "R9" so as to rotate the pulley 55, so that the manipulation wire 19 is hauled and fed out as indicated by arrows in the drawing, along a direction opposite to the above-described direction shown in FIG. 6A. At this time, since the rotation direction of the driving gear 63B is presently coincident with the twisting direction of the wire member 61B at the outermost wire layer (refer to FIG. 4), the rotating forces supplied from the driving motor 29 are firmly transferred to the output-sided gear 59 in high precision.

On the other hand, the driving gear 63A is rotated along a direction "R10", and the rotating forces of this driving gear 63A are transferred via the wire member 61A and the driven gear 65A to the output-sided gear 59. However, in this case, since the rotation direction is opposite to the twisting direction of the wire member 61A at the outermost wire layer, a transfer efficiency is low and the driving forces transferred by the wire member 61B occupy a dominant position.

As previously described, the major driving force transferring path for rotating the output-sided gear 59 becomes any one path of the wire members 61A and 61B, so that on the side of such a transferring path which does not constitute the major driving force transferring path, the function for transferring the rotating forces of the driving motor 29 to the output-sided gear 59 may be alternatively stopped. For instance, the below-mentioned structure may be alternatively realized. That is, while one-way clutches are arranged at the driving gears 63A and 63B respectively, the driving gear 63A may transfer the rotating forces to the wire member 61A only along the direction "R2", whereas the driving gear 63B may transfer the rotating forces to the wire member 61B only along the direction "R7." In this alternative case, loads given to the driving motor 29 may be reduced. Further, one-way clutches may be alternatively provided on the sides of the driven gears 65A and 65B respectively. In this alternative case, manipulating forces applied to the curving manipulation unit 17 (refer to FIG. 4) may be reduced.

Figure 7A:
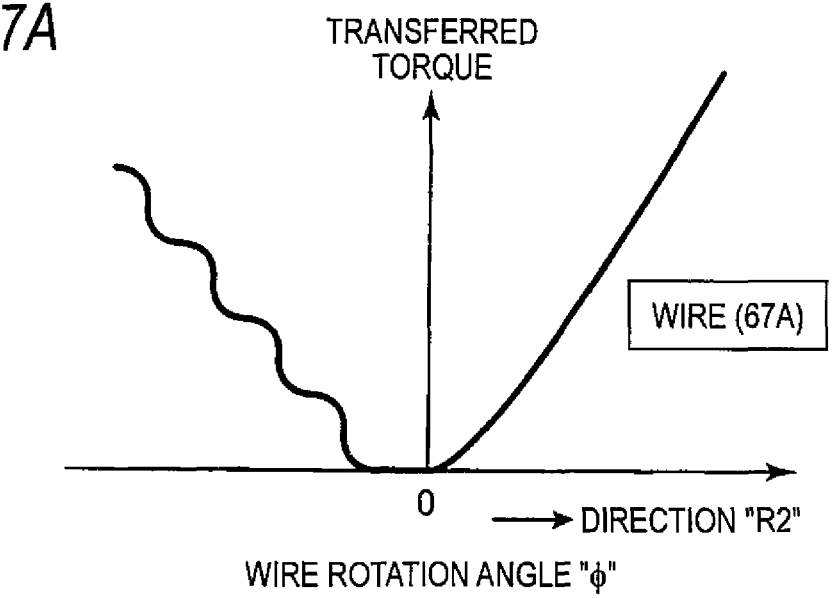
FIG. 7A and FIG. 7B are graphs for representing relationships between wire rotation angles and transferred torque in the case that the respective wire members are solely employed.
Figure 7B:
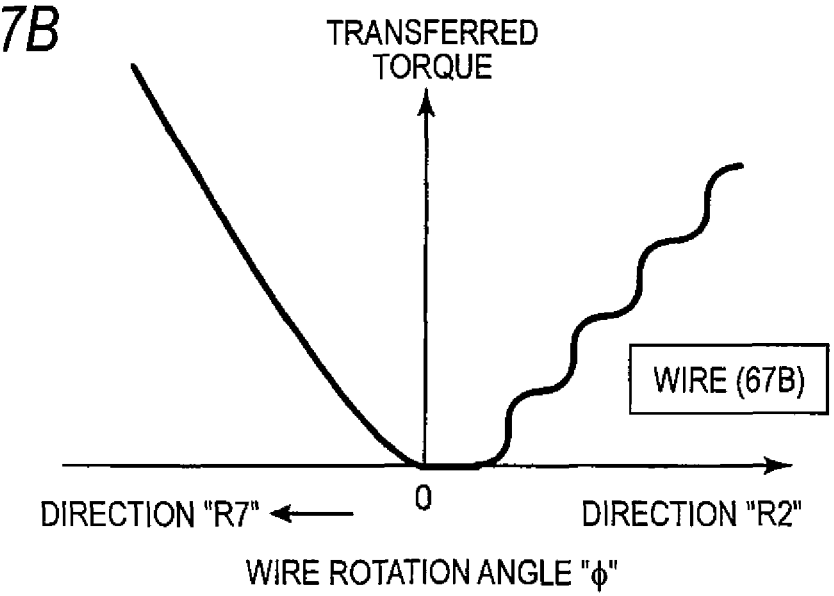

Next, a description is made of a transferring characteristic of the rotating forces produced by the wire members 61A and 61B. FIG. 7A and FIG. 7B are graphs which indicate relationships between wire rotation angles and transferred torque in such a case that each of the wire members 61A and 61B is solely employed. As shown in FIG. 7A, torque generated on the side of the driven gear 65A with respect to a wire rotation angle "φ" applied on the side of the driving gear 63A to the wire 67A shown in FIG. 4 and FIG. 6 has such a characteristic that when the rotation direction is the direction "R2" (twisting direction of wire 67A at outermost layer), the generated torque is increased in a substantially proportional manner, whereas when the rotation direction is the reverse direction with respect to the direction "R2", the generated torque represents a stepped shape, so that the transfer precision of the rotating forces is deteriorated. A transferring characteristic of the wire 67B is similar to the above-described transferring characteristic. That is, as represented in FIG. 7B, torque generated on the side of the driven gear 65B has such a characteristic that when the rotation direction is the direction "R7" (twisting direction of wire 67B at outermost layer), the generated torque is increased in a substantially proportional manner, whereas when the rotation direction is the reverse direction with respect to the direction "R7", the generated torque represents a stepped shape, so that the transfer precision of the rotating forces is deteriorated.

As a consequence, as previously explained, since the rotating forces of the driving motor 29 are transferred by employing at least two sets of wires in a combination manner, the twisting directions of which at the outermost layers thereof are different from each other, such a wire that the twisting direction of the outermost layer thereof is coincident with a rotation direction may become a major driving force transferring wire. As a result, a relationship between rotations of the driving motor 29 and torque to be transferred becomes such a relationship obtained by synthesizing transferring characteristics of the major driving force transferring wires with each other, as indicated in FIG. 8, namely, represents such a substantially proportional relationship that the characteristic of the generated torque does not become the stepped shape along both the normal and reverse rotation directions.

Figure 8:
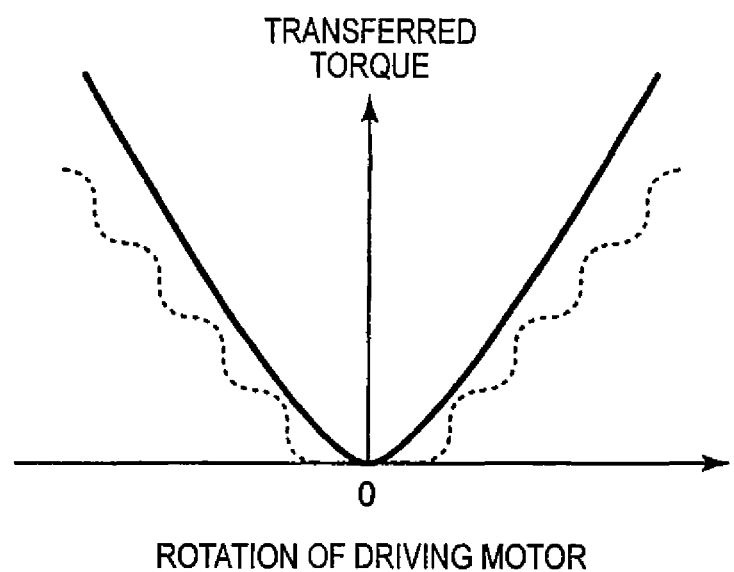
FIG. 8 is a graph for indicating a relationship between rotations of a driving motor and torque to be transferred.

Further, in such a case that the rotating force transferring function as to the side which does not constitute the major driving force transferring path is stopped by employing the above-described one-way clutch, or the like, the linearity of the transferred torque characteristic shown in FIG. 8 may be furthermore improved.

Next, a description is made of a concrete control for applying manipulation assisting power to the curving manipulation unit 17 based upon the above-described structure of the endoscope 100 according to the present embodiment mode.

Figure 9:
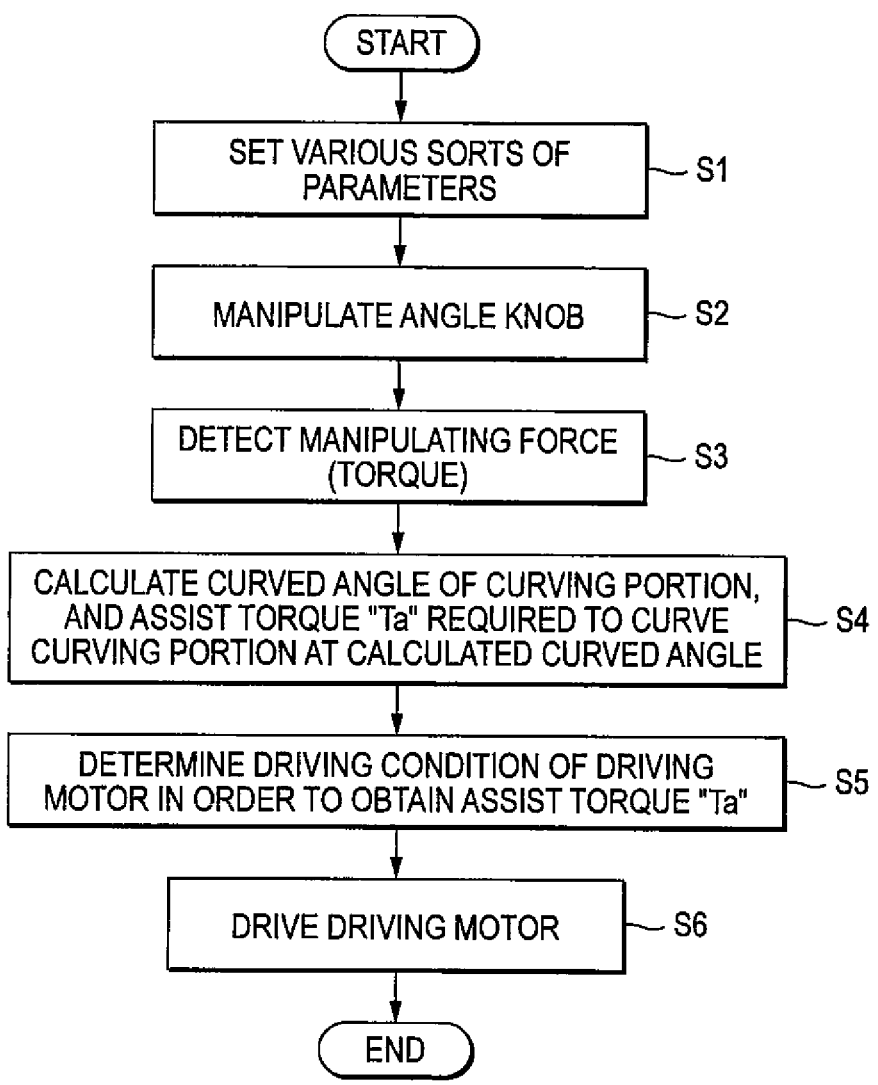
FIG. 9 is a flow chart for describing a sequence for applying manipulation assisting power of the endoscope.

FIG. 9 is a flow chart for describing a sequence for applying the manipulation assisting power of the endoscope 100. When the endoscope 100 is brought into a usable condition, the manipulation assisting power is generated in accordance with the below-mentioned sequence so as to demonstrate the power assist function.

Firstly, various sorts of parameters specific to the above-described endoscope 100 are set to the control unit 23 of the endoscope 100 (S1). The various sorts of parameters contain at least corresponding table information and relationship information. The corresponding table information indicates magnitudes of manipulation assisting power which is generated with respect to manual manipulating forces of an operator, which are detected by the torque sensor 21 shown in FIG. 3. The relationship information represents such a relationship between input electric power of the driving motor 29, and actual manipulation assisting power.

While the former-mentioned corresponding table has been previously stored in the storage unit 39 shown in FIG. 1, a magnitude of assist torque corresponding to manipulation assisting power has been defined with respect to each of curved angles in a relationship between curved angles of the curving portion 11 shown in FIG. 2 and torque required for curving the curving portion 11. The corresponding table information may be arbitrarily set in such a manner that a desirable manipulation characteristic may be obtained for an operator. Alternatively, the corresponding table information may be properly changed in response to contents of manual operations of the endoscope 100 in order to obtain a proper operation characteristic in response to a utilization purpose of the endoscope 100.

On the other hand, the latter-mentioned information of the relationship for the actual manipulation assisting power is determined based upon a sort of the driving motor 29, the driving force transferring mechanism 31, and the like, while an aged deterioration may also occur in the relationship information. In the above-described relationship information, error information about rotation angles between the rotational driving side (namely, input-sided gear 57) of one end side of the wire members 61A and 61B shown in FIG. 4, and the rotating force transferring side (output-sided gear 59) of the other end side.

Next, when the endoscope inserting portion 13 shown in FIG. 3 is inserted into a body cavity of an object under inspection (not shown) and the tip portion 53 thereof is directed to a desirable direction, the operator manually manipulates the angle knobs 49A and 49B functioning as the curving manipulation unit 17 (S2).

A manipulating force applied to the angle knob 49B (similarly applied to angle knob 49A) at this time is detected by the torque sensor 21 (S3). Then, the control unit 23 of the endoscope 100 refers to the table information shown in FIG. 2 from the storage unit 39 so as to calculate a curved angle "θ" of the curving portion 11 corresponding to the detected manipulating force (namely, torque "Tw") and to calculate assist torque "Ta" which is required to curve the curving portion 17 at this calculated curved angle "θ" (S4).

Figure 10:
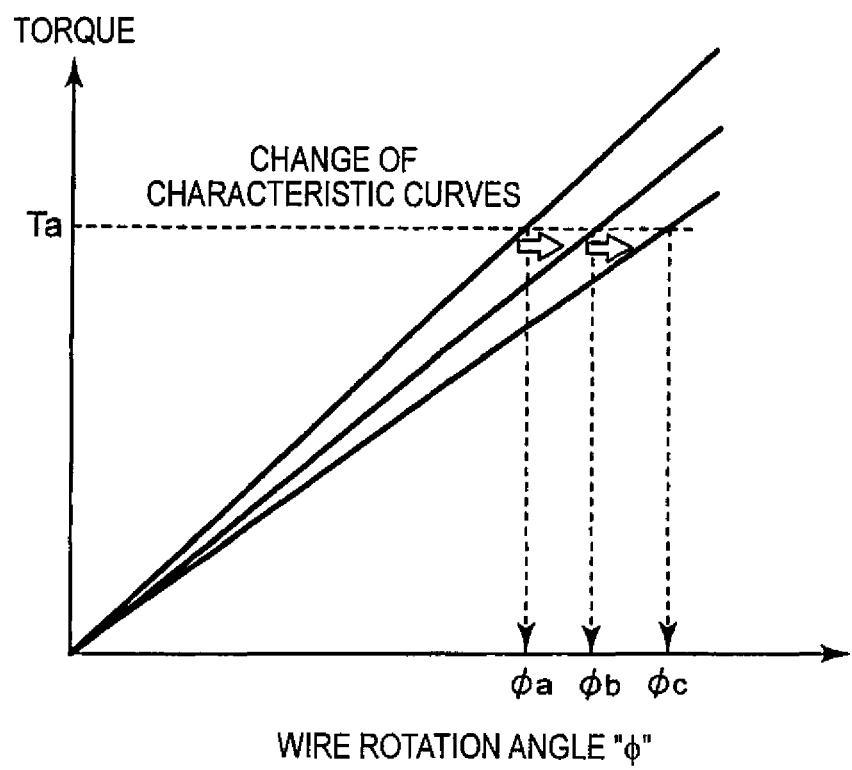
FIG. 10 is a graph for representing a relationship of torque with respect to wire rotation angles.

Then, in order to obtain such a required assist torque "Ta", the control unit 23 determines a drive condition of the driving motor 29 (S5). Concretely speaking, the control unit 23 calculates wire rotation angles "φ" of the wires 67A and 67B at which the required assist torque "Ta" is obtained, and thus, drives the driving motor 29 in such a manner that the calculated wire rotation angles "φ" can be obtained. At this time, as a relationship of torque with respect to wire rotation angles "φ" is represented in FIG. 10, errors are produced in rotation angles due to aged deterioration of the wires 67A and 67B in addition to individual differences of the endoscopes 100. As a result, the wire rotation angle "φ" at which the desirable torque is obtained is calculated by being corrected each time.

In other words, since characteristic curves as to wire rotation angles and generated torque are not always constant but are different from each other in response to use frequencies of an endoscope, a drive condition of the driving motor 29 is determined based upon the latest characteristic curve, and thus, the driving motor 29 is driven under the determined drive condition (S6).

As a result, such torque obtained by synthesizing the assist torque "Ta" generated by driving the driving motor 29 with the torque "Tw" caused by the manipulating force which is actually applied to the curving manipulation unit 17 is applied to the pulley 55. Then, since the manipulation wire 19 is hauled and fed out by pivotally rotating the pulley 55, the curving portion 11 of the endoscope inserting portion 13 is curved, so that the tip portion 53 thereof can be precisely curved at the desirable curved angle.

In accordance with the above-described endoscope 100, the control unit 23 refers to the corresponding table information stored in the storage unit 39 based on the manipulating force produced by the manual operation that is detected by the torque sensor 21 so as to calculate the corresponding manipulation assisting power, and to drive the driving motor 29 based upon the calculated manipulation assisting power, so that this manipulation assisting power can be quickly applied to the manipulating force produced by the manual operation. As a consequence, the required manipulation assisting power can be utilized in higher precision and with superior responsibility, so that superior operability can be achieved.

In this case, it is preferable that characteristic curves represented in FIG. 10 have been previously set before an endoscope is used. For instance, before one endoscope is utilized, a relationship between input electric power to the driving motor 29 and actual manipulation assisting power actually generated by the pulley 55 by operating the driving motor 29 based upon the input electric power has been previously acquired with measurements, and then, characteristic curves defined based upon the acquired information have been previously stored in the storage unit 39. Thereafter, when the above-described endoscope is used, a manipulating force applied to the angle knob 4913 (similarly, manipulating force applied to angle knob 49A) is detected by the torque sensor 21 so as to calculate necessary assist torque "Ta", and input electric power of the driving motor 29 which is required to obtain the calculated assist torque "Ta" is determined based upon the above-described characteristic curve stored in the storage unit 39. As a consequence, proper assist torque can be generated to which the transfer efficiency of the driving force transferring mechanism 31, and variations such as the aged deterioration of the wires 67A and 67B have been considered, so that the endoscope can be continuously driven in higher precision by employing the correction information with respect to the latest condition thereof.

It should be understood that as the input electric power, when the driving motor 29 corresponding to the rotation driving force generating unit is a DC motor, an AC motor, or a servo motor, a voltage value, a current value, and the like may be employed as a control parameter, whereas when the driving motor 29 is a stepper motor, a pulse number, a duty ratio, and the like may be employed as a control parameter. Moreover, the rotation driving force generating unit is not limited only to a motor, but may be replaced by other actuators.

The above-described control of the endoscope can be simultaneously applied with respect to two different directions of the curving portion 11, namely, both the upper/lower curving directions and the right/left curving directions. In this case, the below-mentioned structural mechanisms may be formed in correspondence with the respective angle knobs 49A and 49B. That is, one structural mechanism may be equipped with the torque sensor 21, the pulley 55, the manipulation wire 19, and the driving motor 29, and also, the driving force transferring mechanism 31 and the control unit 23, which are connected to the above-described structural components.

It should also be noted that although the driving motor 29 has been arranged in the LG connector 43 in the above-described example, the driving motor 29 may be alternatively arranged within the video connector 45. Further, in such a case that a plurality of driving motors are used, the plural sets of driving motors may be alternatively arranged by being dispersed to both the LG connector 43 and the video connector 45. In any of these alternative cases, the driving motors may be arranged in simple structures by utilizing connecting connectors which are presently available appendix units within endoscopes.

In addition, while an exclusively-designed appendix unit (not shown) may be separately provided which is connected to the main body manipulating unit 15 via a flexible softened portion, a driving motor may be alternatively arranged within the separately provided appendix unit. In this alternative case, restrictions with respect to sizes and weight of the driving motor and a driving mechanism (not shown) to be connected to the driving motor may be relaxed. As a result, larger manipulation assisting power and more precise manipulation assisting power may be generated.

Also, the control unit 23 and the storage unit 39 represented in FIG. 1 may be arranged within other structural units (for instance, connecting connector 27 etc.) than the main body manipulating unit 15. In addition, since endoscopes may be individually discriminated from each other, the control unit 23 and the storage unit 39 may be alternatively arranged in other structural units such as the light source/signal processing apparatus 35.

Next, a description is made of various modifications of the endoscope 100 having the above-described structure.

Figure 11A:
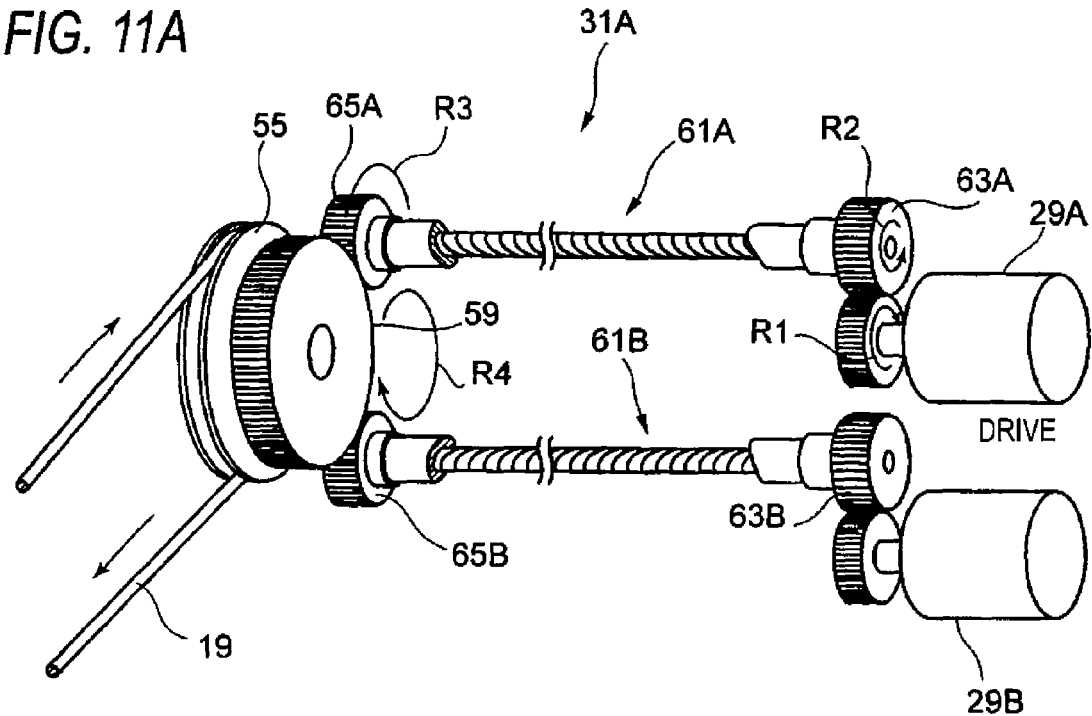
FIG. 11A and FIG. 11B are structural diagrams for showing a structure and an operation example of a driving force transferring mechanism according to a first modification of the present invention.
Figure 11B:
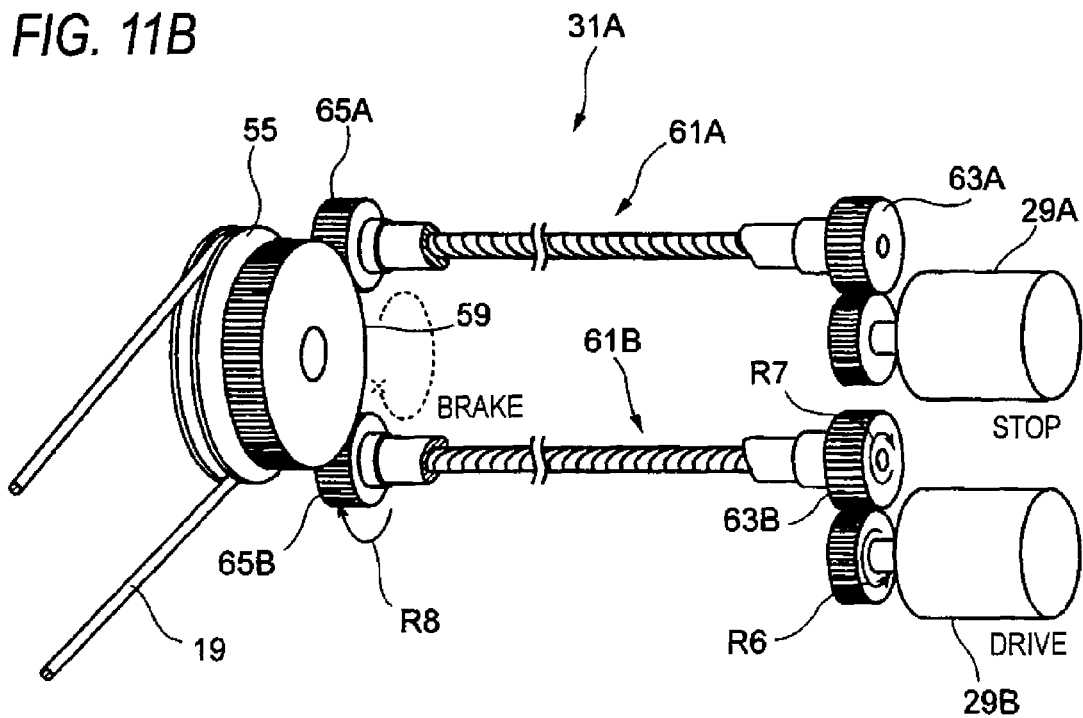

FIG. 11A and FIG. 11B are structural diagrams for showing a structural example and an operational example of a driving force transferring mechanism 31A according to a first modification of the present invention. It should be noted that the same reference numerals shown in FIG. 6 will be employed as those for denoting the same members indicated in FIG. 11A and FIG. 11B.

The driving force transferring mechanism 31A of the first modification is equipped with driving motors 29A and 29B for respective driving gears 63A and 63B. In other words, while the driving force transferring mechanism 31A has the output-sided gear 59 which pivotally rotates the curving manipulation unit 17, the wire members 61A and 61B are connected to the driven gears 65A and 65B which are meshed with the output-sided gear 59. Also, rotation driving shafts of the driving motors 29A and 29B are connected to end portions of the wire members 61A and 61B respectively, which are located opposite to the end portions thereof for connecting the driven gears 65A and 65B.

In accordance with the above-described driving force transferring mechanism 31A, the respective wire members 61A and 61B are separately driven by the driving motors 29A and 29B. As a result, while various sorts of control patterns are previously prepared, these control patterns may be properly applied to the driving force transferring mechanism 31A, so that complex driving operations may be simply realized. For example, as indicated in FIG. 11A, when the output-sided gear 59 is being rotated along the direction "R4" via the wire member 61A by operating the driving motor 29A, as shown in FIG. 11B, the rotations of the driving motor 29A are stopped so as to stop the driving operation of the output-sided gear 59, and moreover, the driving motor 29B is driven along the direction "R6" so as to generate braking forces on the output-sided gear 59 via the wire member 61B. As a consequence, the operations of the pulley 55 and the manipulation wire 19 can be instantaneously stopped. Also, in the case that the output-sided gear 59 is rotated in the reverse direction, braking forces may be similarly generated. As a result, response characteristics of manipulation assisting power to be generated can be increased, so that operability of curving manipulations can be furthermore improved.

Figure 12:
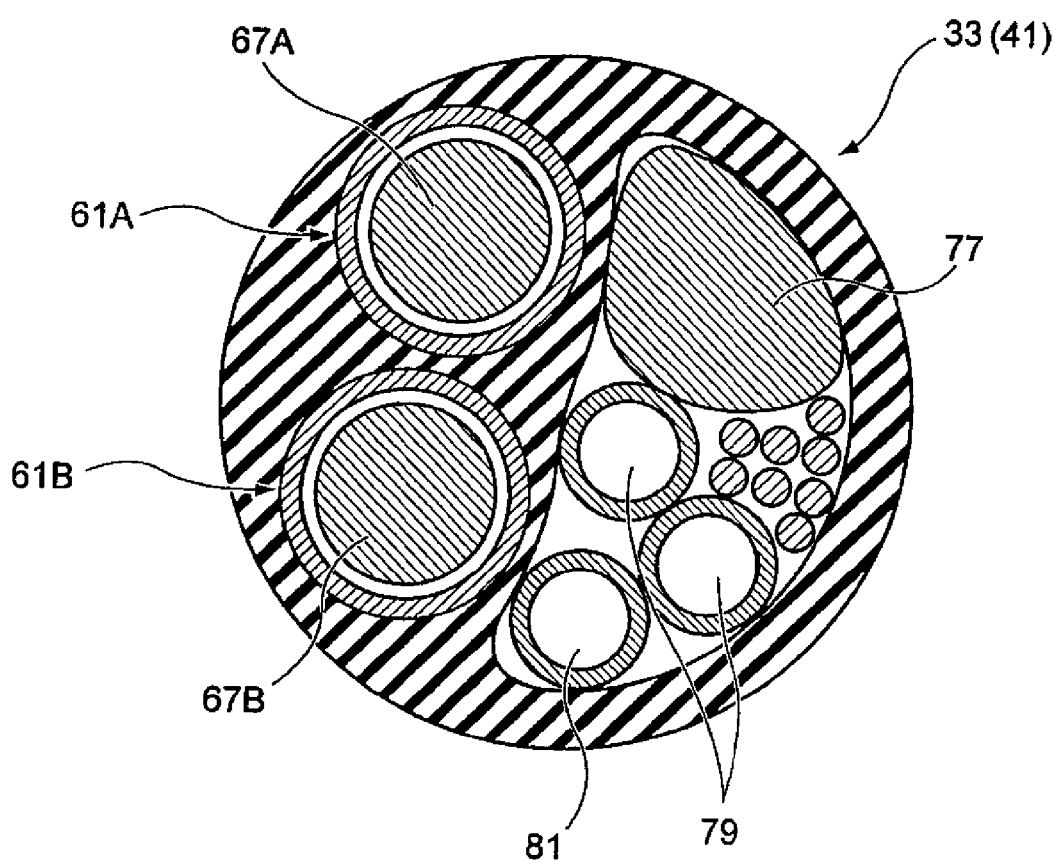
FIG. 12 is a sectional view for indicating a light guide (LG) softened portion as a second modification of the present invention.

FIG. 12 is a sectional view for representing a light guide softened portion 33 according to a second modification of the present embodiment mode.

The LG (Light Guide) softened portion 33 of the second modification corresponds to the universal cord 41 shown in FIG. 3, while outer tubes of the wire members 61A and 61B have been formed by the LG softened portion 33 itself. Generally speaking, a light guide 77 for guiding illumination light, an air feeding/water feeding tube 79 for jetting air and water from a tip of an endoscope inserting portion, a suction tube 81 for performing suction, and cables 83 such as various sorts of signal lines have been internally contained in the LG softened portion 33. If the wire members 61A and 61B having the outer tubes are furthermore assembled in the LG softened portion 33, then it is not possible to avoid that the diameter of the LG softened portion 33 necessarily becomes large.

As a consequence, an outer tube having a relatively large sectional area among the wire members 61A and 61B is formed by the LG softened portion 33 itself. In other words, while a portion of the LG softened portion 33 is utilized as the outer tube, only the wires 67A and 67B are penetrated through the LG softened portion 33, so that the resulting diameter of the LG softened portion 33 can be suppressed to a small diameter and can be constructed in a lower cost.

As previously described, the below-mentioned items have been disclosed in the present specification.

(1) An endoscope includes an endoscope inserting unit, a main body manipulating unit, an appendix unit, a curving manipulation unit, a curving drive unit, a manipulating force detecting unit, a manipulation assisting power calculating unit and a rotation driving force generating unit. The endoscope inserting unit is to be inserted into an inner portion of an object under inspection, and has a freely curvable curving portion in a vicinity of a tip portion of the endoscope inserting unit. The main body manipulating unit is provided to be connected to a base end side of the endoscope inserting unit. The appendix unit is connected via a flexible softened portion to the main body manipulating unit. The curving manipulation unit is provided on the main body manipulating unit, and is manually operated for causing the curving portion to be curved along a direction. The curving drive unit couples the curving manipulation unit to the curving portion so as to curve the curving portion in response to a manipulation performed on the curving manipulation unit. The manipulating force detecting unit detects a manipulating force applied to the curving manipulation unit. The manipulation assisting power calculating unit calculates manipulation assisting power corresponding to the manipulating force detected by the manipulating force detecting unit. The rotation driving force generating unit applies a driving force via a driving force transferring mechanism to the curving drive unit so as to generate the manipulation assisting power calculated by the manipulation assisting power calculating unit. The rotation driving force generating unit is arranged in the appendix unit.

In accordance with the above-described endoscope, since the rotation driving force generating unit is arranged in the appendix unit connected via the softened portion to the main body manipulating unit, even in such a case that performance of the rotation driving force generating unit is increased in order to generate the manipulation assisting power for curving the curving portion with large magnitudes in high precision, the main body manipulating unit is not adversely influenced by that the rotation driving force generating unit is made large and in heavy weight. As a consequence, the main body manipulating unit can apply the manipulation assisting power to the curving drive unit without increasing the size and the weight thereof, while high operability of the main body manipulating unit is maintained. As a consequence, the weight of the main body manipulating unit can be kept light, so that the power assist function having the superior operability and capable of reducing manipulation fatigue of an operator can be achieved.

(2) In the endoscope of the item (1), the driving force transferring mechanism transfers a rotating force of the rotation driving force generating unit in a rotation direction by employing a wire which is formed by twisting a large number of narrow lines. The rotation direction is defined by a twisting direction of a narrow line at the outermost layer within the narrow lines of the wire.

In accordance with the above-described endoscope, since the driving forces are transferred by the wires via the softened portion connected between the appendix unit and the main body manipulating unit, the diameter of the softened portion can be made narrow. Also, since the rotating forces are transferred via the wires capable of withstanding the twisting forces, the angle precision of the rotation driving operation can be increased, and moreover, the aged deterioration of the wires can be reduced.

(3) In the endoscope of the item (2), the wire includes first and second wires. A twisting direction of an outermost layer of the second wire is different from a twisting direction of an outermost layer of the first wire. The driving force transferring mechanism transfers the rotating force by employing at least the first and second wires in a combination manner.

In accordance with the above-described endoscope, even when the rotation direction is any one of the normal rotation direction and the reverse rotation direction, any one of the wires in the twisting direction along which the wire has the stronger resistance with respect to the twist direction transfers the rotating forces, so that the angle precision during the rotary driving operation can be increased even in any one of the rotation directions. Also, the driving force which constitutes the manipulation assisting power is transferred by the plurality of wires, so that the larger driving force can be transferred and the rotation precision can be furthermore increased.

(4) In the endoscope of the item (3), the driving force transferring mechanism includes an input-sided gear, an output-sided gear, a driving gear and a driven gear. The input-sided gear is provided on a rotating drive shaft of the rotation driving force generating unit. The output-sided gear pivotally rotates the curving drive unit. The driving gear is meshed with the input-sided gear. The driven gear is meshed with the output-sided gear.

The input-sided gear is coupled to the output-sided gear by employing plural pieces of the first and second wires. One end side of each of the first and second wires is connected to the driving gear, and the other end side of each of the first and second wires is connected to the driven gear.

In accordance with the above-described endoscope, when the rotation driving force generating unit rotates the input-sided gear, the driving gear meshed with the input-sided gear is rotated, and the driven gear is rotated via the wire joined to the driving gear, so that the output-sided gear is pivotally rotated. As a result, the manipulation assisting power for driving the curving drive unit is generated, so that the curving manipulation of the curving portion is assisted.

(5) In the endoscope of the item (3), the driving force transferring mechanism includes an output-sided gear, a plurality of driven gears and a plurality of rotation driving force generating units. The output-sided gear pivotally rotates the curving manipulation unit. The plurality of the driven gears are meshed with the output-sided gear. The plurality of the rotation driving force generating units are located on the side opposite to the connection sides of the plurality of the driven gears. The plurality of the driven gears are connected to the first and second wires respectively. Rotating drive shafts of corresponding rotation driving force generating units among the plurality of the rotation driving force generating units are connected to end portions of the first and second wires.

In accordance with the above-described endoscope, since the respective wires are driven by the separately prepared rotation driving force generating units, a complex driving operation can be simply realized. For instance, driving of the curving drive unit is stopped by one wire and a braking force is generated by the other wire, so that various modes of control operations can be carried out, for example, the curving drive operation can be instantaneously stopped.

(6) In the endoscope recited in any one of the above-described items (2) to (5), an outer tube is arranged on an outer circumferential portion of the first and second wires, and covers the first and second wires in a freely rotatable manner.

In accordance with the above-described endoscope, since the wire is covered by the outer tube, the wire can firmly transfer the transferred rotating forces to the curving drive unit without interfering with other components.

(7) In the endoscope of the item (6), the outer tube is formed by the softened portion which connects the main body manipulating unit to the appendix unit.

In accordance with the above-described endoscope, since the outer tube is formed by the softened portion itself, a diameter of the softened portion can be suppressed to a small value, so that the resulting endoscope can be arranged in a low cost.

(8) In the endoscope recited in any one of the items (1) to (7), the appendix unit includes a connecting-purpose connector provided with respect to an illuminating apparatus for supplying illumination light to a tip of the endoscope inserting unit.

In accordance with the above-described endoscope, the rotation driving force generating unit is arranged in the connecting-purpose connector for connecting the main body manipulating unit to the illuminating apparatus, so that the rotation driving force generating unit can be arranged in a simple arrangement by utilizing the appendix unit which is presently provided within the endoscope.

(9) In the endoscope recited in any one of the above-described items (1) to (7), the appendix unit includes a connecting-purpose connector provided with respect to a signal processing apparatus for processing an imaging signal outputted from an imaging unit of a tip of the endoscope inserting unit.

In accordance with the above-described endoscope, the rotation driving force generating unit is arranged in the connecting-purpose connector for connecting the main body manipulating unit to the signal processing apparatus, so that the rotation driving force generating unit can be arranged in a simple arrangement by utilizing the appendix unit which is presently provided within the endoscope.

(10) In the endoscope recited in any one of the above-described items (2) to (9), the endoscope further includes a storage unit. The storage unit previously stores thereinto corresponding table information to which the manipulation assisting power calculating unit refers when a manipulation holding force is calculated in response to the detected manipulating force. The corresponding table information indicates a magnitude of manipulation assisting power corresponding to the detected manipulating force.

In accordance with the above-described endoscope, since the manipulation assisting power calculating unit calculates the manipulation assisting power in correspondence with the detected manipulating force by referring to the corresponding table information of the storage unit, the required manipulation assisting power can be firmly generated. Also, since the manipulation assisting power corresponding to the manipulating force applied by the operator can be arbitrarily set by changing the corresponding table information, the magnitude of the manipulation assisting power can be easily adjusted in such a manner that the operator can obtain the superior operability.

(11) In the endoscope of the item (10), the storage unit further stores thereinto information as to a relationship between electric power inputted to the rotation driving force generating unit and actual manipulation assisting power generated by driving the rotation driving force generating unit by the input electric power. The manipulation assisting power calculating unit determines driving electric power of the rotation driving force generating unit based upon the relationship information.

In accordance with the above-described endoscope, the driving electric power for the rotation driving force generating unit is determined based upon the relationship between the electric power inputted to the rotation driving force generating unit and the manipulation assisting power which is actually generated. As a result, the rotation driving force generating unit can be drive-controlled by considering the transfer efficiency of the driving force transferring mechanism, and the like, so that the manipulation assisting power can be applied to the curving drive unit in high precision.

(12) In the endoscope of the item (11), the relationship information contains error information as to a rotation angle between one end side of the wire including a rotation driving side of the wire, and the other end side of the wire including a rotating force transferring side of the wire. The relationship information indicates the relationship between the input electric power to the rotation driving force generating unit and the actual manipulation assisting power.

In accordance with the above-described endoscope, the actual manipulation assisting power is calculated based upon the error information as to the rotation angle, which is caused by aged deterioration of the wire corresponding to the variation factor of the manipulation assisting power, so that the manipulation assisting power can be correctly and simply calculated.

(13) In the endoscope recited in the item (11) or the item (12), the endoscope is further includes an information updating unit. The information updating unit updates the information as to the relationship between the electric power inputted to the rotation driving force generating unit and the actual manipulation assisting power before the endoscope is used. In accordance with the above-described endoscope, the relationship information between the electric power inputted to the rotation driving force generating unit and the actual manipulation assisting power is acquired and the acquired relationship information is updated before the endoscope is used, so that the manipulation assisting power can be generated by continuously employing the information acquired under the latest condition.

(14) In the endoscope recited in any one of the item (1) to the item (13), the curving manipulation unit curves the curving portion by hauling and feeding out one pair of manipulation wires internally inserted along the endoscope inserting unit.

In accordance with the above-described endoscope, the pivotal manipulation of the curving manipulation unit is transferred to the manipulation wires, so that the curving portion can be curved along the desirable direction.

(15) In the endoscope of the item (14), the curving manipulation unit is provided with respect to each of an upper/lower curving direction and a right/left curving direction of the curving portion. The manipulating force detecting unit, the curving drive unit, the manipulation assisting power calculating unit, the driving force transferring mechanism, and the rotation driving force generating unit are provided in correspondence with each of the curving manipulation units. In accordance with the above-described endoscope, the curving manipulation units can be simultaneously driven with respect to each of the upper/lower curving direction and the right/left curving direction of the curving portion, so that the curving manipulation along the arbitrary direction can be carried out in a simple manner.

What is claimed is:

1. An endoscope, comprising:
    an endoscope inserting unit that is to be inserted into an inner portion of an object under inspection and that comprises a freely curvable curving portion in a vicinity of a tip portion of the endoscope inserting unit;
    a main body manipulating unit that is provided to be connected to a base end side of the endoscope inserting unit;
    an appendix unit that is connected via a flexible softened portion to the main body manipulating unit;
    a curving manipulation unit that is provided on the main body manipulating unit and that is manually operated for causing the curving portion to be curved along a direction;
    a curving drive unit that couples the curving manipulation unit to the curving portion so as to curve the curving portion in a response to a manipulation performed on the curving manipulation unit;
    a manipulating force detecting unit that detects a manipulating force applied to the curving manipulation unit;
    a manipulation assisting power calculating unit that calculates a manipulation assisting power corresponding to the manipulating force detected by the manipulating force detecting unit; and
    a rotation driving force generating unit that applies a driving force via a driving force transferring mechanism to the curving drive unit to generate the manipulation assisting power calculated by the manipulation assisting power calculating unit and to apply the manipulation assisting power to the manipulating force applied to the curving manipulation unit,
    wherein the appendix unit comprises the rotation driving force generating unit,
    wherein the driving force transferring mechanism transfers a rotating force of the rotation driving force generating unit in a rotation direction by employing a wire which is formed by twisting a large number of narrow lines,
    wherein the rotation direction is defined by a twisting direction of a narrow line at an outermost layer within the narrow lines of the wire,
    wherein the wire includes first and second wires,
    wherein a twisting direction of an outermost layer of the second wire is different from a twisting direction of an outermost layer of the first wire, and
    wherein the driving force transferring mechanism transfers the rotating force by employing at least the first and second wires in a combination manner.

2. The endoscope according to claim 1, wherein the driving force transferring mechanism includes:
    an input-sided gear which is provided on a rotating drive shaft of the rotation driving force generating unit;
    an output-sided gear which pivotally rotates the curving drive unit;
    a driving gear which is meshed with the input-sided gear; and
    a driven gear which is meshed with the output-sided gear,
    wherein the input-sided gear is coupled to the output-sided gear by employing plural pieces of the first and second wires, and one end side of each of the first and second wires is connected to the driving gear, and
    wherein another end side of each of the first and second wires is connected to the driven gear.

3. The endoscope according to claim 1, wherein the driving force transferring mechanism includes:
    an output-sided gear which pivotally rotates the curving manipulation unit;
    a plurality of driven gears which are meshed with the output-sided gear; and
    a plurality of rotation driving force generating units which are located on a side opposite to the connection sides of the plurality of the driven gears,
    wherein the plurality of the driven gears are connected to the first and second wires respectively, and
    wherein rotating drive shafts of corresponding rotation driving force generating units among the plurality of the rotation driving force generating units are connected to end portions of the first and second wires.

4. The endoscope as according to claim 1, wherein an outer tube is arranged on an outer circumferential portion of the first and second wires, and covers the first and second wires in a freely rotatable manner.

5. The endoscope according to claim 4, wherein the outer tube comprises the softened portion which connects the main body manipulating unit to the appendix unit.

6. The endoscope according to claim 1, wherein the appendix unit includes a connecting-purpose connector provided with respect to an illuminating apparatus for supplying illumination light to a tip of the endoscope inserting unit.

7. The endoscope according to claim 1, wherein the appendix unit includes a connecting-purpose connector provided with respect to a signal processing apparatus for processing an imaging signal outputted from an imaging unit of a tip of the endoscope inserting unit.

8. The endoscope according to claim 1, wherein the curving manipulation unit curves the curving portion by hauling and feeding out one pair of manipulation wires internally inserted along the endoscope inserting unit.

9. The endoscope according to in claim 8, wherein the curving manipulation unit is provided with respect to each of an upper/lower curving direction and a right/left curving direction of the curving portion, and
    wherein the manipulating force detecting unit, the curving drive unit, the manipulation assisting power calculating unit, the driving force transferring mechanism, and the rotation driving force generating unit are provided in correspondence with each of the curving manipulation units.

10. The endoscope according to claim 1, wherein the manipulation assisting power is applied in addition to a force by an operator of the endoscope.

11. The endoscope according to claim 1, wherein the driving force transferring mechanism transfers the rotating force of the rotation driving force generating unit in the rotation direction by employing the first wire and the second wire of said wire.

12. An endoscope, comprising:
- an endoscope inserting unit that is to be inserted into an inner portion of an object under inspection and that comprises a freely curvable curving portion in a vicinity of a tip portion of the endoscope inserting unit;
- a main body manipulating unit that is provided to be connected to a base end side of the endoscope inserting unit;
- an appendix unit that is connected via a flexible softened portion to the main body manipulating unit;
- a curving manipulation unit that is provided on the main body manipulating unit and that is manually operated for causing the curving portion to be curved along a direction;
- a curving drive unit that couples the curving manipulation unit to the curving portion so as to curve the curving portion in a response to a manipulation performed on the curving manipulation unit;
- a manipulating force detecting unit that detects a manipulating force applied to the curving manipulation unit;
- a manipulation assisting power calculating unit that calculates a manipulation assisting power corresponding to the manipulating force detected by the manipulating force detecting unit;
- a rotation driving force generating unit that applies a driving force via a driving force transferrin mechanism to the curving drive unit to venerate the manipulation assisting power calculated by the manipulation assisting power calculating unit and to apply the manipulation assisting power to the manipulating force applied to the curving manipulation unit,
  - wherein the appendix unit comprises the rotation driving force generating unit,
  - wherein the driving force transferring mechanism transfers a rotating force of the rotation driving force generating unit in a rotation direction by employing a wire which is fainted by twisting a large number of narrow lines, and
  - wherein the rotation direction is defined by a twisting direction of a narrow line at an outermost layer within the narrow lines of the wire; and
- a storage unit that previously stores thereinto a corresponding table information to which the manipulation assisting power calculating unit refers when a manipulation holding force is calculated in a response to the detected manipulating force,
- wherein the corresponding table information indicates a magnitude of a manipulation assisting power corresponding to the detected manipulating force.

13. The endoscope according to claim 12, wherein the storage unit further stores thereinto information as to a relationship between an electric power inputted to the rotation driving force generating unit and an actual manipulation assisting power generated by driving the rotation driving force generating unit by the input electric power, and
- wherein the manipulation assisting power calculating unit determines driving electric power of the rotation driving force generating unit based upon the relationship information.

14. The endoscope according to claim 13, wherein the relationship information contains error information as to a rotation angle between one end side of the wire including a rotation driving side of the wire, and another end side of the wire including a rotating force transferring side of the wire, and
- wherein the relationship information indicates the relationship between the input electric power to the rotation driving force generating unit and the actual manipulation assisting power.

15. The endoscope according to claim 13, further comprising:
- an information updating unit that updates the information as to the relationship between the electric power inputted to the rotation driving force generating unit and the actual manipulation assisting power before the endoscope is used.

16. An endoscope, comprising:
- an endoscope inserting unit that is to be inserted into an inner portion of an object under inspection and that comprises a freely curvable curving portion in a vicinity of a tip portion of the endoscope inserting unit;
- a main body manipulating unit that is provided to be connected to a base end side of the endoscope inserting unit;
- an appendix unit that is connected via a flexible softened portion to the main body manipulating unit;
- a curving manipulation unit that is provided on the main body manipulating unit and that is manually operated for causing the curving portion to be curved along a direction;
- a curving drive unit that couples the curving manipulation unit to the curving portion so as to curve the curving portion in a response to a manipulation performed on the curving manipulation unit;
- a manipulating force detecting unit that detects a manipulating force applied to the curving manipulation unit;
- a manipulation assisting power calculating unit that calculates a manipulation assisting power corresponding to the manipulating force detected by the manipulating force detecting unit;
- a rotation driving force generating unit that applies a driving force via a driving force transferrin mechanism to the curving drive unit to generate the manipulation assisting power calculated by the manipulation assisting power calculating unit and to apply the manipulation assisting power to the manipulating force applied to the curving manipulation unit, wherein the appendix unit comprises the rotation driving force generating unit; and
- a storage unit that stores a corresponding table information to which the manipulation assisting power calculating unit refers when a manipulation holding force is calculated in a response to the detected manipulating force.

17. The endoscope according to claim 16, wherein the corresponding table information indicates a magnitude of a manipulation assisting power corresponding to the detected manipulating force.

* * * * *